United States Patent [19]
Berg

[11] Patent Number: 5,597,455
[45] Date of Patent: Jan. 28, 1997

[54] SEPARATION OF 3-CARENE AND LIMONENE BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 586,179

[22] Filed: Jan. 16, 1996

[51] Int. Cl.$^6$ .................. B01D 3/40; C07C 7/08
[52] U.S. Cl. ................. 203/57; 203/60; 203/63; 203/64; 203/65; 203/69; 585/350; 585/860; 585/864; 585/866
[58] Field of Search ................ 203/57–58, 60, 203/63, 65, 64, 69; 585/350, 867, 860, 864, 865, 866, 862

[56] References Cited

U.S. PATENT DOCUMENTS

| | | | |
|---|---|---|---|
| 2,459,433 | 1/1949 | Johnson et al. | 203/65 |
| 3,422,029 | 1/1969 | Booth | 212/364 |
| 5,380,405 | 1/1995 | Berg | 203/57 |
| 5,391,264 | 2/1995 | Berg | 203/57 |
| 5,441,608 | 8/1995 | Berg | 203/51 |

*Primary Examiner*—Virginia Manoharan

[57] ABSTRACT

3-Carene and limonene cannot be separated from each other by rectification because of the closeness of their boiling points. They are readily separated by extractive distillation. Effective agents are: diethylene glycol phenyl ether, nonyl phenol, tripropylene glycol methyl ether, ethyl salicylate, 4-ethylphenol and 2-phenoxyethanol.

1 Claim, No Drawings

5,597,455

SEPARATION OF 3-CARENE AND LIMONENE BY EXTRACTIVE DISTILLATION

FIELD OF THE INVENTION

This invention relates to a method of separating 3-carene, limonene and phellandrene using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the-highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table i shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 28 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of terpenes, e.g. turpentine. A process to separate this mixture into its pure components would enhance its value. Three of the commonest close boiling compounds in one of these are 3-carene, B.P.=167° C. phellandrene, B.P.=175° C. and limonene, B.P.=178° C. The relative volatility among these three is as low as 1.05 which makes it impossible to separate by conventional rectification. Extractive distillation would be an attractive method of effecting the separation of these three if agents can be found that (1) will create a large apparent relative volatility among these three and (2) are easy to recover from the extractive agent. Table 2 shows the relative volatility required to obtain 99% purity. With an agent giving a relative volatility of 1.75, only 23 actual plates are required.

TABLE 2

Theoretical and Actual Plates Required vs. Relative Volatility for Terpene Separation

| Relative Volatility | Theoretical Plates Required At Total Reflux, 99% Purity | Actual Plates Required 75% Efficiency |
|---|---|---|
| 1.4 | 28 | 38 |
| 1.6 | 20 | 27 |
| 1.75 | 17 | 23 |

OBJECTIVE OF THE INVENTION

The object of this invention is to provide a process or method of extractive distillation that will enhance the relative volatility of 3-carene, limonene and phellandrene in their separation in a rectification column. It is a further object of this invention to identify organic compounds which in addition to the above constraints, are stable, can be separated from the terpenes and recycled to the column with little decomposition.

SUMMARY OF THE INVENTION

The objects of this invention are provided by a process for separating 3-carene, limonene and phellandrene which entails the use of certain organic compounds as the agent in extractive distillation.

DETAILED DESCRIPTION OF THE INVENTION

I have discovered that certain organic compounds will greatly improve the relative volatility between 3-carene, limonene and phellandrene and permit the separation by rectification when employed as the agent in extractive distillation. Table 3 lists the compounds that I have found to be effective in separating 3-carene from limonene in the presence of phellandreene. They are methyl heptanoate, dibutyl phthalate, 3-isopropyl phenol, o-cresol, 2,6-dimethyl phenol, o-sec. butyl phenol, nitrobenzene, 3-nitrotoluene, adiponitrile, diethylene glycol ethyl ether, salicylaldehyde and 2-phenyl phenol.

Table 4 lists the compounds that are effective in separating 3-carene from limonene. They are ethyl salicylate, dibutyl phthalate, 4-ethyl phenol, 3-isopropyl phenol, o-sec. butyl phenol, 4-nitrotoluene, nonyl phenol, 2-phenoxy ethanol, diethylene glycol phenyl ether and tripropylene glycol methyl ether.

Table 5 lists the compounds that are effective in separating phellandrene from 3-carene and limonene. They are propyl benzoate, ethylene glycol diacetate, diethyl maleate, methyl salicylate, dibutyl phthalate, diethyl succinate, 1-octanol, phenethyl alcohol, 2-undecanone, 2-pyrrolidone, 2-pyrrolidinone, 1-(2-hydroxyethyl)-2-pyrrolidinone, 2-tert. butyl phenol, nonyl phenol, 2-undecanol, diethylene glycol butyl ether, diethylene glycol ethyl ethers, diethylene glycol hexyl ether, salicylaldehyde, m-cresol, p-cresol, 4-phenyl phenol and 4-fluoro-1,1-biphenyl.

TABLE 3

Effective Extractive Distillation Agents For Separating 3-Carene from Limonene and Phellandrene

| Agent | Temp. °C. | Rel. Vol. 3-Car/Lim |
|---|---|---|
| Methyl heptanoate | 168 | 1.35 |
| Dibutyl phthalate | 170 | 1.35 |
| 3-Isopropyl phenol | 180 | 1.5 |
| o-Cresol | 170 | 1.3 |
| 2,6-Dimethyl phenol | 178 | 1.3 |
| o-sec. Butyl phenol | 180 | 1.3 |
| Nitrobenzene | 178 | 1.3 |
| 3-Nitrotoluene | 181 | 1.3 |
| Adiponitrile | 170 | 1.3 |
| Diethylene glycol ethyl ether | 173 | 1.45 |
| Salicylaldehyde | 170 | 1.3 |
| o-Cresol - 2-Phenyl Phenol | 170 | 1.35 |

TABLE 4

Effective Extractive Distillation Agents For Separating 3-Carene From Limonene

| Agent | Temp. °C. | Rel. Vol. 3-Car/Lim |
|---|---|---|
| Ethyl salicylate | 187 | 1.3 |
| Dibutyl phthalate | 180 | 1.35 |
| 4-Ethyl phenol | 169 | 1.3 |
| 3-Isopropyl phenol | 187 | 1.3 |
| o-sec. Butyl phenol | 179 | 1.35 |
| 4-Nitrotoluene | 175 | 1.3 |
| Nonyl phenol | 179 | 1.55 |
| 2-Phenoxyethanol | 174 | 1.45 |
| Diethylene glycol phenyl ether | 179 | 1.6 |

TABLE 5

Effective Extractive Distillation Agents For Separating Phellandrene From 3-Carene And Limonene

| Agent | Temp. °C. | Rel. Vol. Ph/Lim |
|---|---|---|
| Propyl benzoate | 183 | 1.6 |
| Ethylene glycol diacetate | 169 | 1.3 |
| Diethyl maleate | 180 | 1.35 |
| Methyl salicylate | 182 | 1.3 |
| Dibutyl phthalate | 170 | 1.5 |
| Diethyl succinate | 181 | 1.3 |
| 1-Octanol | 174 | 1.5 |
| Phenethyl alcohol | 178 | 1.45 |
| 2-Undecanone | 185 | 1.3 |
| 2-Pyrrolidone | 173 | 1.3 |
| 2-Pyrrolidinone | 170 | 2.0 |
| 1-(2-Hydroxyethyl)-2-pyrrolidinone | 171 | 1.9 |
| 2-tert.-Butyl phenol | 181 | 1.4 |
| Nonyl phenol | 178 | 1.3 |
| Diethylene glycol butyl ether | 180 | 1.8 |
| 2-Undecanol | 186 | 1.4 |
| Diethylene glycol ethyl ether | 173 | 1.65 |
| Diethylene glycol hexyl ether | 180 | 1.7 |
| Salicylaldehyde | 170 | 1.4 |

TABLE 5-continued

Effective Extractive Distillation Agents For Separating Phellandrene From 3-Carene And Limonene

| Agent | Temp. °C. | Rel. Vol. Ph/Lim |
|---|---|---|
| m-p-Cresol, 4-Phenyl phenol | 170 | 1.6 |
| 4-Fluoro-1,1-biphenyl | 186 | 1.35 |

THE USEFULNESS OF THE INVENTION

The usefulness or utility of this invention can be demonstrated by referring to the data presented in Tables 3, 4 and 5. All of the successful agents show that 3-carene, limonene and phellandrene can be separated from each other by means of extractive distillation in a rectification column and that the ease of separation as measured by relative volatility is considerable.

WORKING EXAMPLES

1. Fifty grams of a 3-carene, limonene, phellandrene mixture and 50 grams of diethylene glycol ethyl ether were charged to a vapor-liquid equilibrium still and refluxed for seven hours. The vapor composition was 54.6% 3-carene, 31.9% limonene and 13.5% phellandrene; the liquid composition was 40.7% 3-carene, 34.9% limonene and 24.4% phellandrene. This indicates a relative volatility of 3-carene to limonene of 1.45 and limonene to phellandrene of 1.65.
2. Fifteen grams of 3-carene, 35 grams of limonene and 50 grams of nonyl phenol were charged to the vapor-liquid equilibrium still and refluxed for two hours. The vapor composition was 37.6% 3-carene, 62.4% limonene; the liquid composition was 28.1% 3-carene and 71.9% limonene. This indicates a relative volatility of 1.55.
3. Fifty grams of a 3-carene, limonene, phellandrene mixture and 50 grams of diethylene glycol butyl ether were charged to the vapor-liquid equilbrium still and refluxed for four hours. The vapor composition was 71.1% 3-carene, 12.9% limonene and 16% phellandrene; the liquid composition was 63.8% 3-carene, 11.2% limonene and 25% phelladrene. This indicates a relative volatility of limonene to phellandrene of 1.8 and of 3-carene to limonene of 0.97.

What is claimed is:

1. A method for recovering 3-carene from a mixture consisting of 3-carene and limonene which consists essentially of distilling said mixture consisting of 3-carene and limonene in the presence of an extractive distillation agent, recovering the 3-carene as overhead product and obtaining the limonene and the extractive distillation agent as bottoms product, wherein said extractive distillation agent consists of one material selected from the group consisting of ethyl salicylate, dibutyl phthalate, 4-ethyl phenol, 3-isopropyl phenol, o-sec. butyl phenol, 4-nitrotoluene, nonyl phenol, diethylene glycol phenyl ether, tripropylene glycol methyl ether and 2-phenoxyethanol.

* * * * *